(12) United States Patent
Jaax et al.

(10) Patent No.: US 9,409,022 B2
(45) Date of Patent: *Aug. 9, 2016

(54) METHODS AND SYSTEMS FOR STIMULATING A MOTOR CORTEX OF THE BRAIN TO TREAT A MEDICAL CONDITION

(75) Inventors: Kristen N. Jaax, Saugus, CA (US); Todd K. Whitehurst, Santa Clarita, CA (US); Rafael Carbunaru, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 13/050,836

(22) Filed: Mar. 17, 2011

(65) Prior Publication Data

US 2011/0166546 A1   Jul. 7, 2011

Related U.S. Application Data

(63) Continuation of application No. 12/685,161, filed on Jan. 11, 2010, now Pat. No. 7,962,219, and a continuation of application No. 11/067,286, filed on Feb. 25, 2005, now Pat. No. 7,657,316.

(51) Int. Cl.
*A61N 1/00* (2006.01)
*A61N 1/36* (2006.01)
*A61N 1/372* (2006.01)

(52) U.S. Cl.
CPC ......... *A61N 1/36082* (2013.01); *A61N 1/37205* (2013.01)

(58) Field of Classification Search
CPC .................... A61N 1/36082; A61N 1/37205
USPC ........................................................... 607/45
See application file for complete search history.

(56) References Cited

U.S. PATENT DOCUMENTS

| | | |
|---|---|---|
| 4,856,526 A | 8/1989 | Liss et al. |
| 5,193,539 A | 3/1993 | Schulman et al. |
| 5,193,540 A | 3/1993 | Schulman et al. |
| 5,312,439 A | 5/1994 | Loeb |
| 5,540,734 A | 7/1996 | Zabara |
| 5,938,688 A | 8/1999 | Schiff |
| 6,051,017 A | 4/2000 | Loeb et al. |
| 6,164,284 A | 12/2000 | Schulman et al. |
| 6,185,452 B1 | 2/2001 | Schulman et al. |
| 6,208,894 B1 | 3/2001 | Schulman et al. |
| 6,366,813 B1 | 4/2002 | DiLorenzo |
| 6,405,079 B1 | 6/2002 | Ansarinia |

(Continued)

OTHER PUBLICATIONS

Hargreaves, et al. "Pathophysiology of Migraine—New Insights", Canadian Journal of Neurological Sciences, Nov. 1999, 26: Suppl. 3-S12-S19 (8 pages).

(Continued)

*Primary Examiner* — Mallika D Fairchild
(74) *Attorney, Agent, or Firm* — Lowe Graham Jones PLLC; Bruce E. Black

(57) ABSTRACT

Methods of treating a medical condition include applying at least one stimulus to a motor cortex within a brain of a patient with an implanted system control unit in accordance with one or more stimulation parameters. Systems for treating a medical condition include a system control unit implanted within the patient that is configured to apply at least one stimulus to a motor cortex within a brain of a patient in accordance with one or more stimulation parameters.

1 Claim, 11 Drawing Sheets

(56) References Cited

U.S. PATENT DOCUMENTS

| | | |
|---|---|---|
| 6,484,059 B2 | 11/2002 | Gielen |
| 6,591,138 B1 | 7/2003 | Fischell et al. |
| 6,735,475 B1 | 5/2004 | Whitehurst et al. |
| 7,010,351 B2 | 3/2006 | Firlik et al. |
| 7,013,177 B1 | 3/2006 | Whitehurst et al. |
| 7,529,586 B2 | 5/2009 | Wahlstrand et al. |
| 7,590,454 B2 | 9/2009 | Garabedian et al. |
| 7,627,383 B2 | 12/2009 | Haller et al. |
| 7,657,316 B2 | 2/2010 | Jaax et al. |
| 7,657,317 B2 | 2/2010 | Thacker et al. |
| 2006/0195154 A1 | 8/2006 | Jaax et al. |
| 2006/0241717 A1 | 10/2006 | Whitehurst et al. |
| 2007/0179558 A1 | 8/2007 | Gliner et al. |
| 2010/0114192 A1 | 5/2010 | Jaax et al. |

OTHER PUBLICATIONS

Hamel, "Current concepts of migraine pathophysiolgoy", Canadian Journal of Neurological Sciences, vol. 6, Suppl. A, Autumn 1999 (6 pages).

May, et al., "The Trigeminovascular System in Humans: Pathophysiologic Implications for Primary Headache Syndromes of the Neural Influences on the Cerebral Circulation", Journal of Cerebral Blood Flow and Metabolism, 19:115-127, Feb. 1999 (13 pages).

Friedman, et al., "Intraoral Chilling versus Oral Sumatriptan for Acute Migraine", Heart Disease, Nov.-Dec. 2001, 3:357-361 (5 pages).

Salvesen, "Cluster Headache", Current Treatment Options in Neurology, Nov. 1999, 1:441-449 (9 pages).

Walker et al., "Regulation of Limbic Motor Seizures by GABA and Glutamate Transmission in Nucleus Tractus Solitarius" Epilepsia, 40(8):1051-1057, Aug. 1999 (7 pages).

Menetrey, et al. "Spinal and trigeminal projections to the nucleus of the solitary tract: a possible substrate for somatovisceral and viscerovisceral reflex activation", J. Comp. Neurol., Jan. 15, 1987, 255(3): 439-50 (12 pages).

Fanselow, et al., "Reduction of pentylenetetrazole-induced seizure activity in awake rats by seizure-triggered trigeminal nerve stimulation", Journal of Neuroscience, Nov. 1, 2000, 20(21):8160-8168 (9 pages).

METHODS AND SYSTEMS FOR STIMULATING A MOTOR CORTEX OF THE BRAIN TO TREAT A MEDICAL CONDITION

RELATED APPLICATIONS

The present application is a continuation of U.S. patent application Ser. No. 12/685,161, filed Jan. 11, 2010, which is a continuation of U.S. patent application Ser. No. 11/067,286, filed Feb. 25, 2005, now issued as U.S. Pat. No. 7,657,316, which are incorporated herein by reference.

BACKGROUND

The public health significance of many medical, psychiatric, and neurological conditions and/or disorders is often overlooked, probably because of their episodic nature and the lack of mortality attributed to them. However, some medical conditions, such as headaches and facial pain, are often incapacitating, with considerable impact on social activities and work, and may lead to significant consumption of drugs.

Headaches are one of the most common ailments, and afflict millions of individuals. The specific etiology of headaches may be difficult to pinpoint. Known etiology of headache pain include trauma and vascular, autoimmune, degenerative, infectious, drug and medication-induced, inflammatory (sarcoid), neoplastic (primary or metastatic), metabolic-endocrine, iatrogenic (such as post-surgical), musculoskeletal and myofascial causes. Even if the condition underlying the headache pain is identified and treated, headache pain may still persist.

Diagnosis of headache pain will typically include an identification of one or more categories of headaches. There are a variety of different headaches with different features. Migraine headaches, as defined by the International Headache Society (IHS) Classification, are typically unilateral, throbbing headaches lasting from four to seventy-two hours. Migraines are often accompanied by nausea, vomiting, light sensitivity and/or noise sensitivity. Females suffer from migraines more than males by an approximate ratio of 3:1. Migraine headaches can be further subdivided and sub-classified into a number of different categories, such as, but not limited to, for example, migraine with aura, migraine without aura, transformed migraine, and retinal migraine.

Migraines have traditionally been treated with medications to prevent their recurrence and to alleviate acute pain and associated symptoms, such as nausea and vomiting. Non-invasive modalities of migraine treatment, which may be used alone or in combination, have included: diet modification, which may include the avoidance of known headache triggers (such as certain foods); biofeedback and relaxation techniques as well as other psychological modalities; acupuncture; chiropractic manipulation; and physical therapy. Invasive therapeutic procedures have also been implemented and have included localized anesthetic blocks as well as neurosurgical interventions, such as nerve and ganglion transections and/or resections. However, use of those invasive techniques has typically been reserved for patients who have been unable to tolerate non-invasive procedures or who suffer from refractory headaches inadequately controlled with non-invasive methods. Invasive techniques are not more readily employed because they have been known to cause undesirable side effects and pose risks of infection and/or physiological damage to nerve tissues.

Currently, the highest known success rate (approximately seventy percent) in alleviating the pain of an acute migraine attack has been achieved using triptan class medications. Unfortunately, the effectiveness of each therapeutic modality typically varies widely between individual migraine sufferers and, irrespective of the treatment modality used, the suppression of migraine pain is often short-lived, with the pain recurring at levels which are typically less but sometimes equally or rarely more intense than before treatment. Many migraine sufferers find that their migraines are resistant to conventional treatment. In some cases, patients suffer from migraines on a continuous daily basis rather than on an episodic basis. Accordingly, a major emphasis for migraine treatment has been on prevention techniques.

Newer methods for treating a variety of neurological disorders have included various electrical stimulation techniques. For example, U.S. Pat. No. 5,540,734 to Zabara describes a suggested therapeutic modality for a variety of medical, psychiatric and neurological disorders, including migraines, in which modulating electrical signals are applied to either or both of the trigeminal and glossopharyngeal nerves using electrodes. The principle behind these approaches is to disrupt or modulate abnormal neuronal transmissions in the nervous system through the application of the modulating electrical signals.

Cluster headaches are so termed due to their repeated occurrence in groups or clusters. Cluster headaches are much less common than migraines. Migraine sufferers outnumber cluster headache sufferers by a ratio of approximately 100:1. Cluster headaches are characterized by intense, stabbing pain usually starting in the region of an eye or temple and localizing to one side of the face. Autonomic features such as lacrimation, nasal congestion, ptosis, conjunctival injection and pupillary changes are common in cluster headaches, which occur predominantly (approximately 90%) in males and usually start in the third or fourth decade of life. It is believed that the ingestion of alcohol may trigger the onset of cluster headaches.

IHS criteria indicate that episodic attacks of cluster headaches may last up to 90 minutes and may occur as many as six times per day. Cluster headaches typically occur in cycles lasting weeks to months and then spontaneously remit. Frequently, cluster headaches have a seasonal correlation, with their onset occurring more often in the fall and spring. While there are wide variations in the start of cluster headache cycles between headache sufferers, the cycles experienced by individual headache sufferers frequently follow a defined pattern with little deviation. The headaches usually occur at night, and often awaken the headache sufferer from sleep. It is not unusual for individual headache sufferers to experience the onset of cluster headaches at the same time during the night over repeated nights.

Because of the typically short duration of cluster headaches, therapies designed to abort the pain of an acute attack must have a quick onset of action. Such therapies have included oxygen inhalation and injections of medication, such as dihydro ergotamine (DHE), ketorolac, or sumatriptan. Non-invasive therapies used to treat cluster headache pain and prevent their recurrence have included use of medications including ergot derivatives, varapamil, lithium, steroids, and sodium valproate; psychological intervention with biofeedback and relaxation techniques; and acupuncture. Anesthetic agents (such as Lidocaine) have been applied to the sphenopalatine ganglia, either directly, using a syringe, or indirectly, by soaking a long cotton swab in the anesthetic and placing the swab intranasally adjacent to the sphenopalatine ganglia, such that the anesthetic diffuses through the nasal mucosa to affect the SPG. Invasive approaches for the treatment of cluster headaches have included localized anesthetic block, surgical resection, radiofrequency, alcohol/phenol infiltration, radiosurgery and cryotherapy of the sphenopalatine ganglia and the trigeminal nerve and ganglion. The invasive approaches for treating cluster headaches are typically used only in headache sufferers who cannot tolerate the non-invasive methods of treatment or in whom the cluster headaches are refractory and inadequately controlled with non-invasive methods.

Neuralgias, such as trigeminal, sphenopalatine, and occipital neuralgias, may start at any age, although trigeminal neuralgia is more common among the elderly. From a pathophysiological standpoint, neuralgias, which are types of pain associated with a particular nerve, always originate from and are transmitted by the involved nerve. Accordingly, neuralgias may be caused by direct injury to nerves in the form of trauma, infection (such as herpes), neuroma formation or demyelination. The pain of a neuralgia may be brief and paroxysmal or continuous, and numerous attacks may occur throughout the day. Neuralgias do not feature seasonal or diurnal patterns in the onset of pain. In contrast to cluster headaches, trigeminal neuralgia often has an associated "trigger zone" on the face which can trigger the onset of the pain. Sphenopalatine neuralgia often has autonomic features that are not commonly found in other neuralgias. In occipital neuralgia, the occipital nerve is usually tender to palpation and pain can be manifested anywhere along the course of the nerve.

Neuralgias, like migraines, have been treated using medication, invasive procedures, and, rarely, electrical stimulation of cranial nerves which are part of the central nervous system. None of the medications used in treating neuralgias have generally been effective in treating cluster headaches, other than sodium valproate.

The use of medications to treat the above-described conditions and other types of medical, psychiatric, and neurological conditions and/or disorders can result in systemic side-effects of wide-ranging severity. Invasive techniques used to destroy tissues, such as lesioning, resecting, freezing, or burning, are typically non-reversible, and the treatment cannot be adjusted once applied. Destruction of the nerve tissue may itself lead to significant side effects, such as deafferentation pain.

SUMMARY

Methods of treating a medical condition include applying at least one stimulus to a motor cortex within a brain of a patient with an implanted system control unit in accordance with one or more stimulation parameters.

Systems for treating a medical condition include a system control unit implanted within the patient that is configured to apply at least one stimulus to a motor cortex within a brain of a patient in accordance with one or more stimulation parameters.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1A:
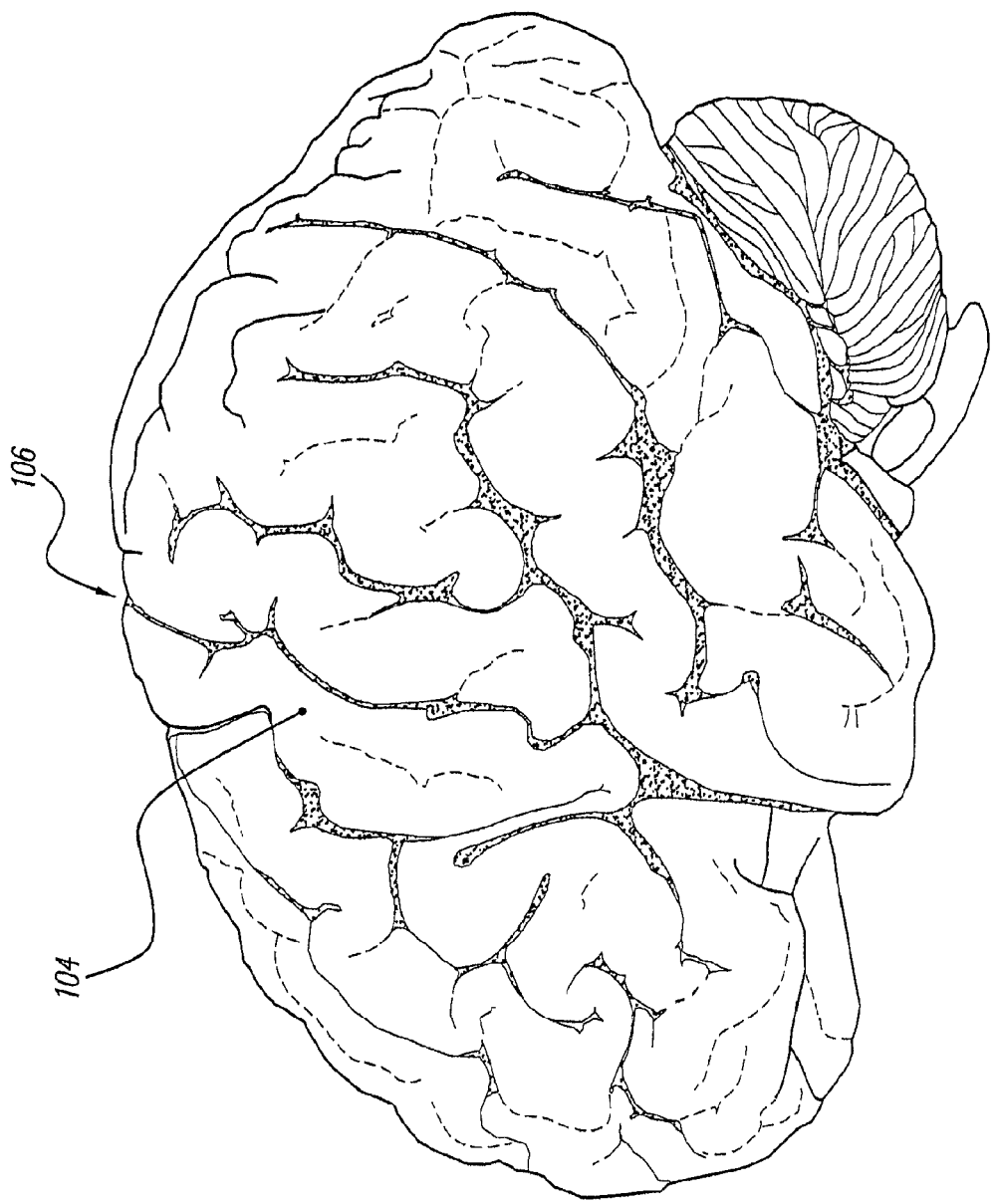
FIG. 1A depicts the lateral surface of the brain according to principles described herein.

Methods and systems for treating many different types of medical, psychiatric, and neurological conditions and/or disorders of varying degrees are described herein. A system control unit (SCU) is implanted adjacent to the motor cortex within the brain of a patient. The SCU is configured to apply at least one stimulus to the motor cortex in accordance with one or more stimulation parameters. The stimulus is configured to treat one or more medical, psychiatric, and/or neurological conditions and/or disorders. The treatment may include electrical stimulation, drug stimulation, or both. Consequently, as used herein and in the appended claims, the term "stimulus" or "stimulation," unless otherwise indicated, will broadly refer to either an electrical stimulation, a drug stimulation, or both.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As will be described in more detail below, there exist many different types of medical, psychiatric, and neurological conditions and/or disorders of varying degrees for which researchers have found potential causes. However, the exact causes of many medical, psychiatric, and neurological conditions and disorders remain unknown. Consequently, many techniques have been presented to treat these conditions and disorders. These techniques have had varying levels of success. Potential causes and treatments for some medical conditions will be discussed below, including headaches, facial pain, and epilepsy. However, it will be recognized that headaches, facial pain, and epilepsy are merely illustrative of the many different types of medical, psychiatric, and neurological conditions and disorders that exist and may be treated according to the principles described herein.

Headache and Facial Pain

The mechanism of a migraine is not well understood. Prevalent theories suggest that a migraine is a central nervous system neurovascular disorder and that the trigeminal nerve may play a prominent role. The trigeminal nerve carries virtually all of the sensation from the face, and thus it likely plays a role in any pain felt at the front or the top of the head.

In "Pathophysiology of migraine—new insights" (*Canadian Journal of Neurological Sciences*, November 1999), Hargreaves, et al. state that "the exact nature of the central dysfunction that is produced in migraines is still not clear and may involve spreading depression-like phenomena and activation of brainstem monoaminergic nuclei that are part of the central autonomic, vascular, and pain control centers. It is generally thought that local vasodilation of intracranial extracerebral blood vessels and a consequent stimulation of surrounding trigeminal sensory nervous pain pathways is a key mechanism underlying the generation of headache pain associated with migraine. This activation of the trigeminovascular system is thought to cause the release of vasoactive sensory neuropeptides, especially CGRP, that increase the pain response. The activated trigeminal nerves convey nociceptive information to central neurons in the brain stem trigeminal sensory nuclei that in turn relay the pain signals to higher centers where headache pain is perceived. It has been hypothesized that these central neurons may become sensitized as a migraine attack progresses." The disorder of migraine may ultimately evoke changes in blood vessels within pain-producing intracranial meningeal structures that give rise to headache pain.

Hargreaves, et al. further state that "the 'triptan' anti-migraine agents (e.g., sumatriptan, rizatriptan, zolmitriptan, and naratriptan) are serotonergic agonists that have been shown to act selectively by causing vasoconstriction through 5 HT1B receptors that are expressed in human intracranial arteries and by inhibiting nociceptive transmission through an action at 5-HT1D receptors on peripheral trigeminal sensory nerve terminals in the meninges and central terminals in brainstem sensory nuclei. These three complementary sites of action underlie the clinical effectiveness of the 5 HT1B/1D agonists against migraine headache pain and its associated symptoms."

In "Current concepts of migraine pathophysiology" (*Canadian Journal of Neurological Sciences*, Autumn 1999), Hamel cites evidence that indicates migraine originates in the brain and, in its process and evolution, affects the meningeal blood vessels and leads to the development of head pain. Hamel states that "this manifestation is related to the activation of the trigeminovascular sensory nerves, which release neuropeptides that mediate vasodilation, and the proinflammatory reaction thought to be involved in pain generation and transmission. Such a concept underscores the fact that the relationship between the nerves and the blood vessels is of paramount importance in the manifestation of the disease's symptoms."

It has also been suggested that primary headache syndromes, such as cluster headache and migraine, share an anatomical and physiologic substrate, namely the neural innervation of the cranial circulation. In "The Trigeminovascular System in Humans: Pathophysiologic Implications for Primary Headache Syndromes of the Neural Influences on the Cerebral Circulation" (*Journal of Cerebral Blood Flow Metabolism*, February 1999), May, et al. report that observations of vasodilation were made in an experimental trigeminal pain study. They conclude that the observed dilation of these vessels in trigeminal pain is not inherent to a specific headache syndrome, but rather is a feature of the trigeminal neural innervation of the cranial circulation. They also state that clinical and animal data suggest that the observed vasodilation is, in part, an effect of a trigeminoparasympathetic reflex.

They suggest that the trigeminal innervation of the cranial circulation and the observed vasodilation of the associated vasculature during headache syndromes may be an underlying pathophysiological mechanism of headache.

In "Intraoral Chilling versus Oral Sumatriptan for Acute Migraine" (*Heart Disease*, November-December 2001), Friedman, et al. state that "recent evidence suggests that the primary inflammation occurs in the maxillary nerve segment [of the trigeminal nerve], accessible intraorally. Local tenderness, related to symptom laterality, has been palpated in asymptomatic migraine patients."

In "Cluster Headache" (*Current Treatment Options in Neurology*, November 1999), Salvesen suggests a possible link between the trigeminal nerve and cluster headache: "for a very limited group of patients with chronic cluster headache, surgery may be a last resort. The best surgical options are probably radio-frequency rhizotomy or microvascular decompression of the trigeminal nerve."

In a recent study involving eighteen patients, fifteen patients obtained immediate pain relief from chronic intractable cluster headaches after one or two injections of percutaneous retrogasserian glycerol rhizolysis. However, cluster headache recurred in seven patients over the course of the study, suggesting that permanent trigeminal destruction may not be an effective treatment.

For many years, Transcutaneous Electrical Nerve Stimulation (TENS) has been applied with some success to the control of headache and facial pain symptoms. TENS is used to modulate the stimulus transmissions by which pain is felt by applying low-voltage electrical stimulation to large peripheral nerve fibers via electrodes placed on the skin. A study of 282 migraineurs had patients undergo Punctual (i.e., episodic) Transcutaneous Electrical Nerve Stimulation (PuTENS) via pocket electrostimulators. After more than 6 months PuTENS was prophylactically effective in eighty percent of the patients in the study, i.e., their frequency of attacks and use of drugs were reduced by at least fifty percent. However, TENS devices can produce significant discomfort and can only be used intermittently.

Epilepsy

Recent studies in both developed and developing countries have shown that up to 70 percent of newly diagnosed children and adults with epilepsy can be successfully treated (i.e., complete control of seizures for several years) with antiepileptic drugs. After two to five years of successful treatment, drugs can be withdrawn in about 70 percent of children and 60 percent of adults without the patient experiencing relapses. However, up to 30 percent of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patients may have a seizure focus in the hippocampi bilaterally. However, both hippocampi cannot be removed without adversely affecting a patient's long-term memory. Other patients may have a seizure focus that lies adjacent to a critical area such as the speech center.

Vagus nerve stimulation (VNS) has been applied with partial success in patients with refractory epilepsy. In this procedure, an implantable pulse generator (IPG) is implanted in the patient's thorax, and an electrode lead is routed from the IPG to the left vagus nerve in the neck. Based on a number of studies, approximately five percent of patients undergoing VNS are seizure-free, and an additional 30-40 percent of patients have a greater than 50 percent reduction in seizure frequency.

In addition to this relatively low efficacy, VNS may lead to significant side effects. The vagus nerve provides parasympathetic innervation to the cardiac tissue, and thus VMS may lead to bradycardia, arrhythmia, or even graver cardiac side effects. In fact, VNS systems may only be used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

The exact mechanism of seizure suppression using VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker, et al. ("Regulation of limbic motor seizures by GABA and glutamate transmission in nucleus tractus solitarius," *Epilepsia*, August 1999) applied muscimol, an agonist of the inhibitory neurotransmitter GABA, to the NTS in a murine model of epilepsy. Muscimol applied to the NTS attenuated seizures in all seizure models tested, whereas muscimol applied to adjacent regions of NTS had no effect. Additionally, biculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. conclude that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nuclei) receives somatic sensory input from all cranial nerves, with much of its input coming from the vagus nerve.

Convincing evidence has been given that a significant number of neurons in the trigeminal nerve project to the NTS. By applying horseradish peroxidase to peripheral branches of the trigeminal nerve in a cat, it was found that branches of the trigeminal nerve (the lingual and pterygopalatine nerves) were found to contain fibers which ended ipsilaterally in the rostral portions of the NTS, massively in the medial and ventrolateral NTS, moderately in the intermediate and interstitial NTS, and sparsely in the ventral NTS. (The rostralmost part of the NTS was free from labeled terminals.) After injecting the enzyme into the NTS portions rostral to the area postrema, small neurons were scattered in the maxillary and mandibular divisions of the trigeminal ganglion. It was concluded that trigeminal primary afferent neurons project directly to the NTS. By staining for substance P immunoreactivity, it was found that Substance P containing trigeminal sensory neurons project to the NTS.

Convincing evidence has also been reported that a significant number of neurons in the trigeminal nuclei project to the NTS. Menetrey, et al used the retrograde transport of a protein-gold complex to examine the distribution of spinal cord and trigeminal nucleus caudalis neurons that project to the NTS in the rat. [See Menetrey, et al. "Spinal and trigeminal projections to the nucleus of the solitary tract: a possible substrate for somatovisceral and viscerovisceral reflex activation." *J Comp Neurol* 1987 Jan. 15; 255(3):439-50.] The authors found that retrogradely labeled cells were numerous in the superficial laminae of the trigeminal nucleus caudalis, through its rostrocaudal extent. Since the NTS is an important relay for visceral afferents from both the glossopharyngeal and vagus nerves, the authors suggest that the spinal and trigeminal neurons that project to the NTS may be part of a larger system that integrates somatic and visceral afferent inputs from wide areas of the body. The projections may underlie somatovisceral and/or viscerovisceral reflexes, perhaps with a significant afferent nociceptive component.

Another study utilized microinfusion and retrograde transport of D [3H] aspartate to identify excitatory afferents to the NTS. The authors found that the heaviest labeling was localized bilaterally in the trigeminal nucleus with cells extending through its subdivisions and the entire rostrocaudal axis.

In addition, a study by Fanselow, et al. ("Reduction of pentylenetetrazole-induced seizure activity in awake rats by seizure-triggered trigeminal nerve stimulation," *Journal of Neuroscience*, November 2000) demonstrated that unilateral stimulation via a chronically implanted nerve cuff electrode applied to the infraorbital branch of the trigeminal nerve led to a reduction in electrographic seizure activity of up to 78 percent. The authors reported that bilateral trigeminal stimulation was even more effective.

The thalamus is believed to play a major role in some types of epilepsy by acting as a center for seizure onset or as a relay station in allowing a focal seizure to propagate. In a Single Positron Emission Computed Tomography (SPECT) study of patients with left-sided VNS systems, a consistent decrease of activity was found in the left thalamus caused by VNS. The authors concluded that left-sided VNS reduces seizure onset or propagation through inhibition of the thalamic relay center.

Thalamic relay neurons are essential in generating 3 Hz absence seizures and are believed to be involved in other types of epilepsy. Thalamic nuclei of some patients suffering from epilepsy display neuronal activities described as "low-threshold calcium spike bursts," which have been shown to be related to a state of membrane hyperpolarization of thalamic relay neurons. This thalamic rhythmicity is transmitted to the related cortex, thanks to thalamocortical resonant properties. In the cortex, an asymmetrical corticocortical inhibition (edge effect) at the junction between low and high frequency zones is proposed to be at the origin of a cortical activation of high frequency areas bordering low frequency ones.

Other Medical, Psychiatric, and Neurological Conditions and Disorders

Other medical, psychiatric, and neurological conditions and/or disorders include, but are not limited to, the following:

1) Pain resulting from one or more medical conditions including, but not limited to: migraine headaches, including but not limited to migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; musculoskeletal neck pain; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia.

2) Epilepsy, including, but not limited to, generalized and partial seizure disorders.

3) Cerebrovascular diseases resulting from one or more medical conditions including, but not limited to, atherosclerosis, aneurysms, strokes, and cerebral hemorrhage.

4) Autoimmune diseases resulting from one or more medical conditions including, but not limited to, multiple sclerosis.

5) Sleep disorders resulting from one or more medical conditions including, but not limited to, sleep apnea and parasomnias.

6) Autonomic disorders resulting from one or more medical conditions including, but not limited to: gastrointestinal disorders, including, but not limited to, gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including, but not limited to, cardiac dysrythmias and arrythmias, hypertension, and carotid sinus disease.

7) Urinary bladder disorders resulting from one or more medical conditions including, but not limited to, spastic and flaccid bladder.

8) Abnormal metabolic states resulting from one or more medical conditions including, but not limited to, hyperthyroidism and hypothyroidism.

9) Disorders of the muscular system resulting from one or more medical conditions including, but not limited to, muscular dystrophy and spasms of the upper respiratory tract and face.

10) Neuropsychiatric disorders resulting from one or more medical conditions including, but not limited to, depression, schizophrenia, bipolar disorder, autism, personality disorders, and obsessive-compulsive disorder.

11) Movement disorders of any type.

12) Chronic pain caused disease, compression or entrapment, direct trauma, penetrating injuries, contusions, fractured or dislocated bones, tumors, intraneural hemorrhages, exposure to cold or radiation, prolonged use of crutches, staying in one position for too long, and any other type of pressure involving any peripheral nerve such as the ulnar, radial, or peroneal nerves.

For ease of explanation, the term "medical condition" will be used herein and in the appended claims, unless otherwise specifically denoted, to refer to any medical, psychiatric, and/or neurological condition and/or disorder described herein, listed above, or related or similar to any condition or disorder described or listed herein.

Figure 1B:
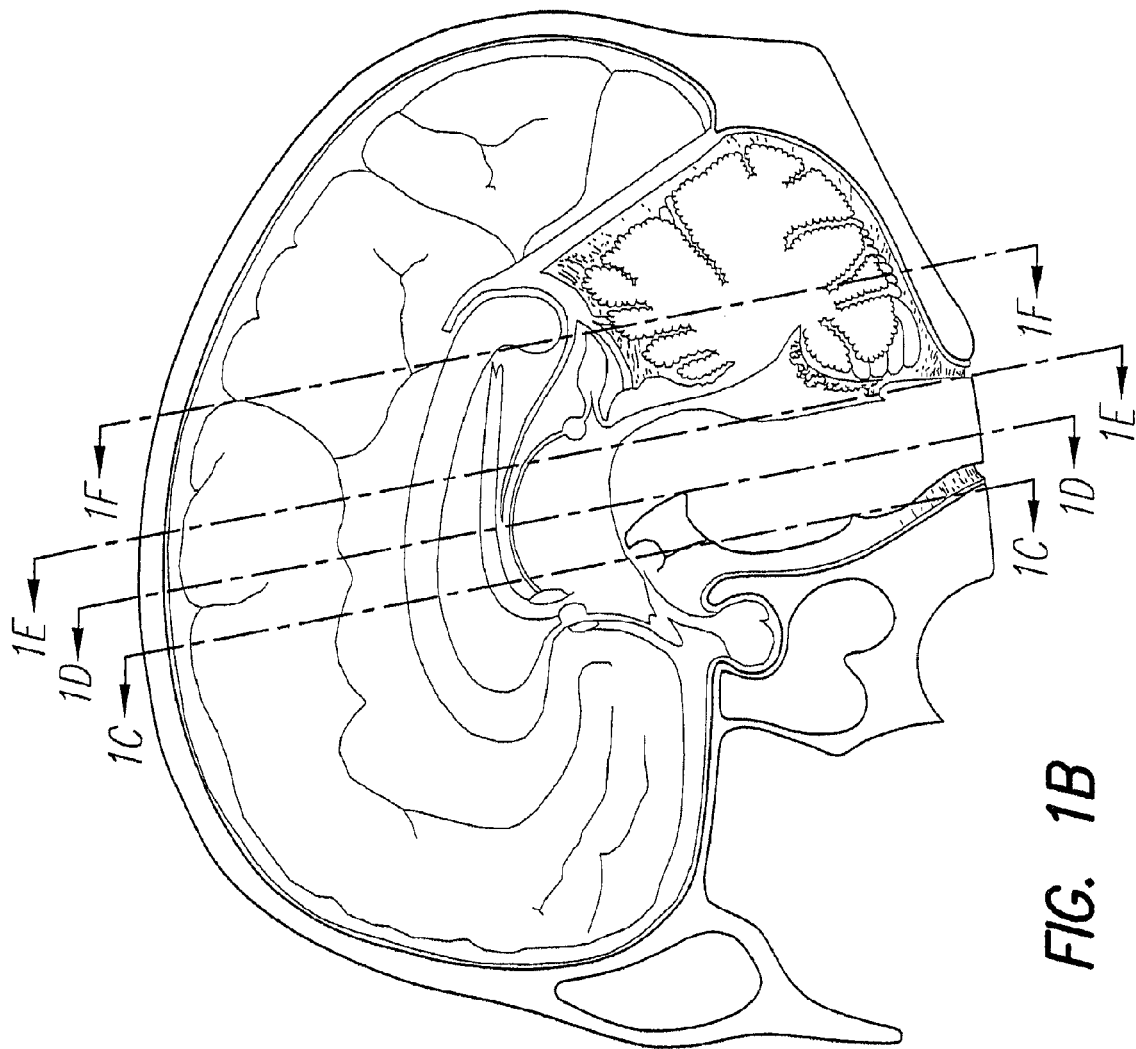
FIG. 1B depicts the medial surface of the head according to principles described herein.
Figure 1C:
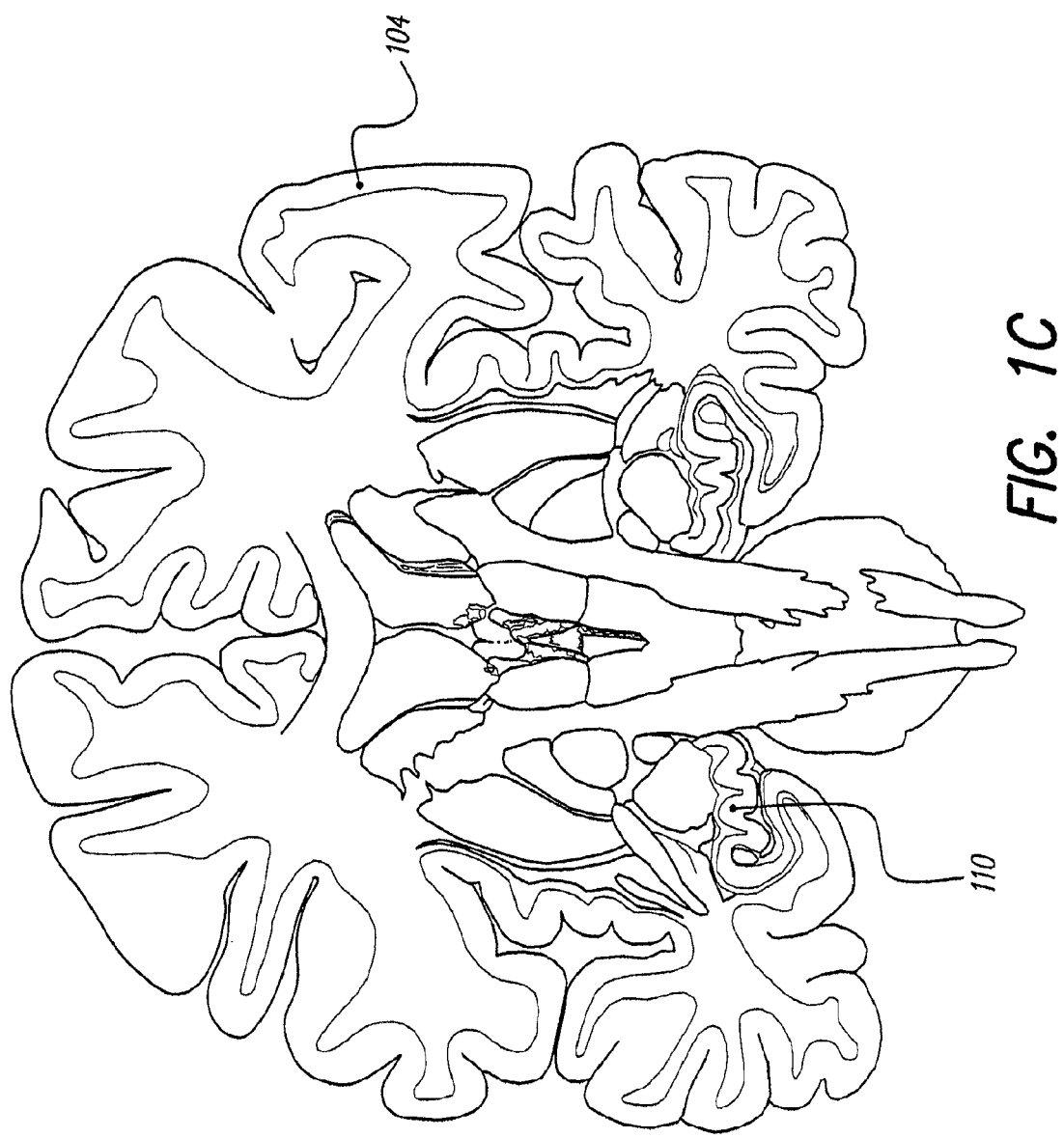
FIGS. 1C-1F are coronal section views of the brain taken in cross-section along the lines indicated in FIG. 1B according to principles described herein.
Figure 1D:
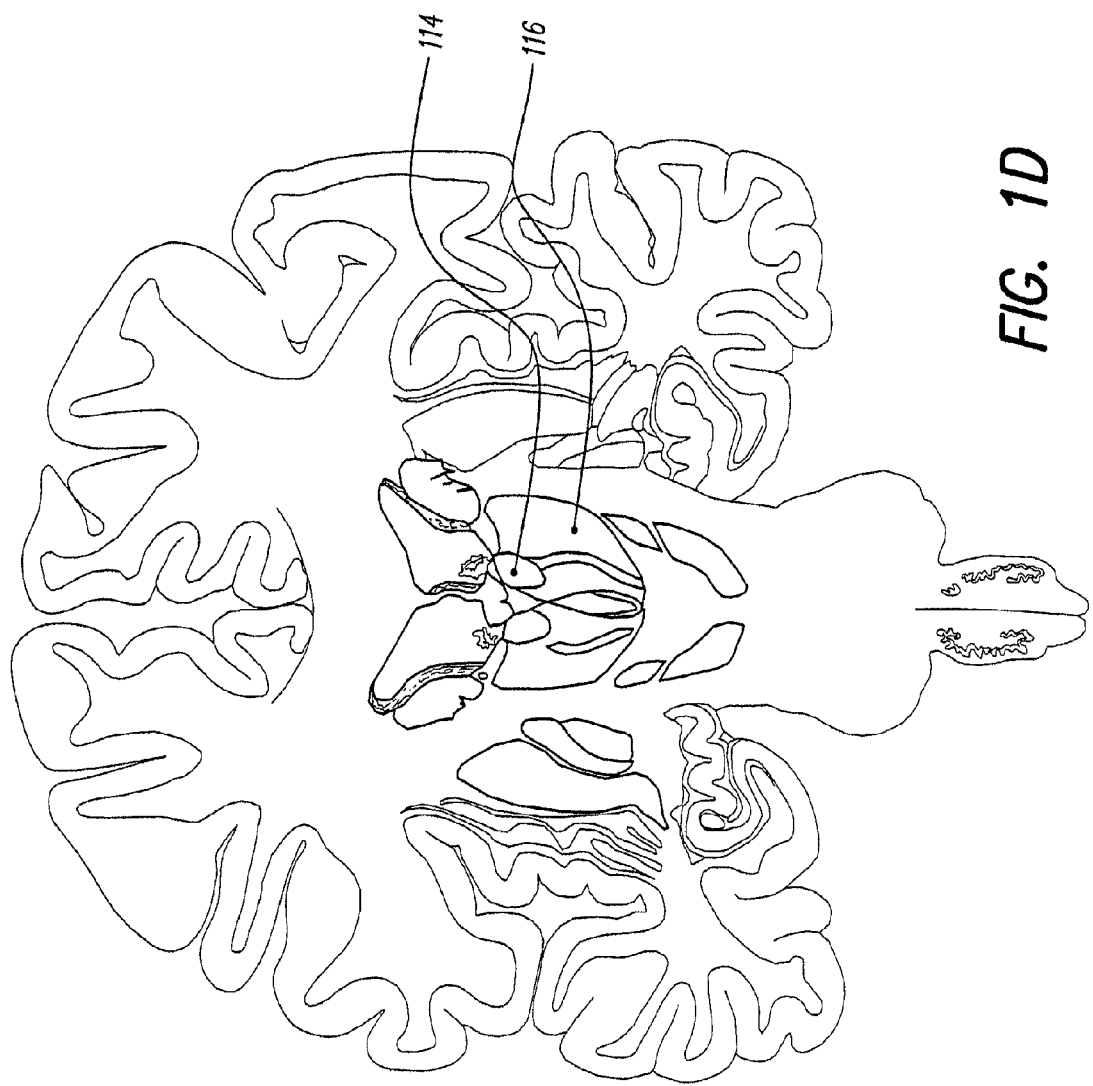
Figure 1E:
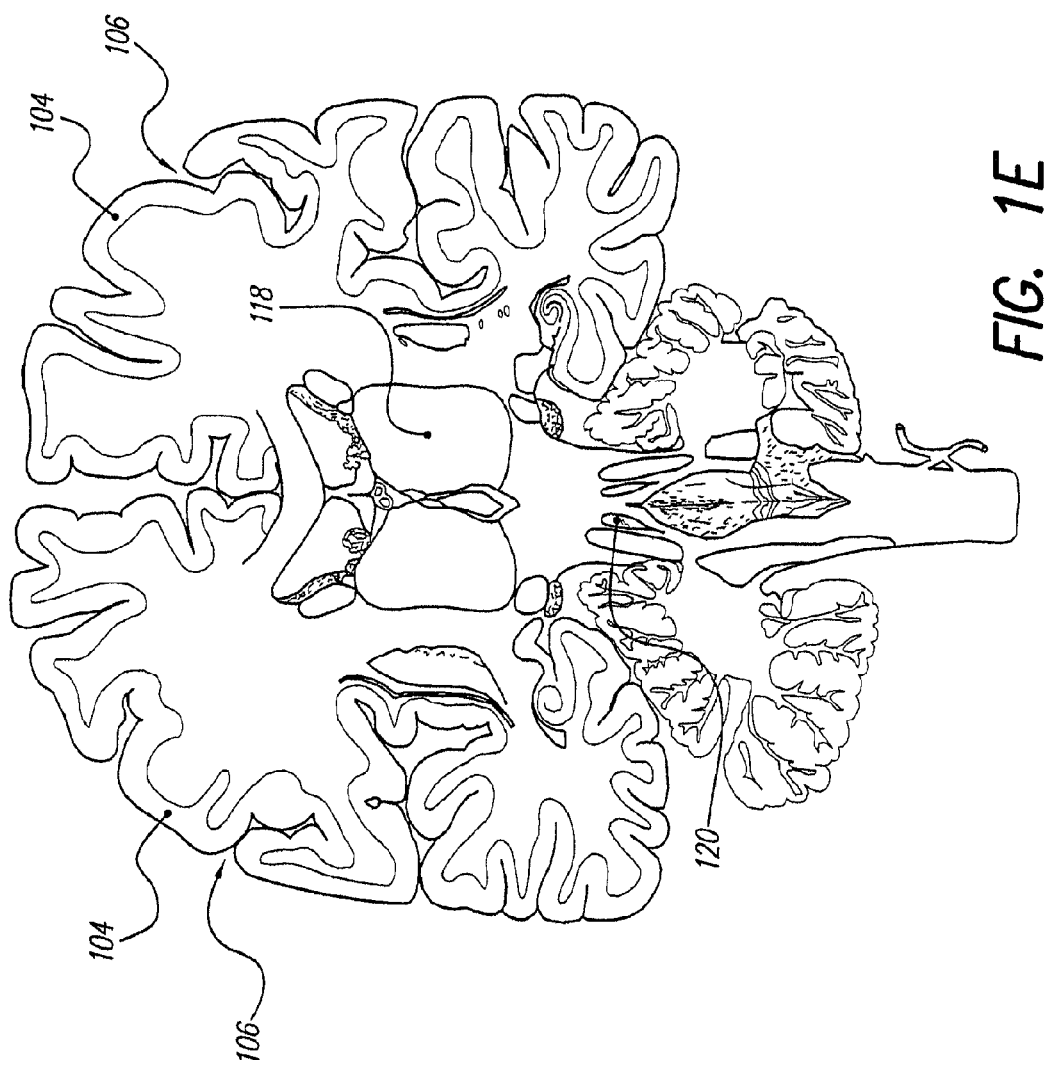
Figure 1F:
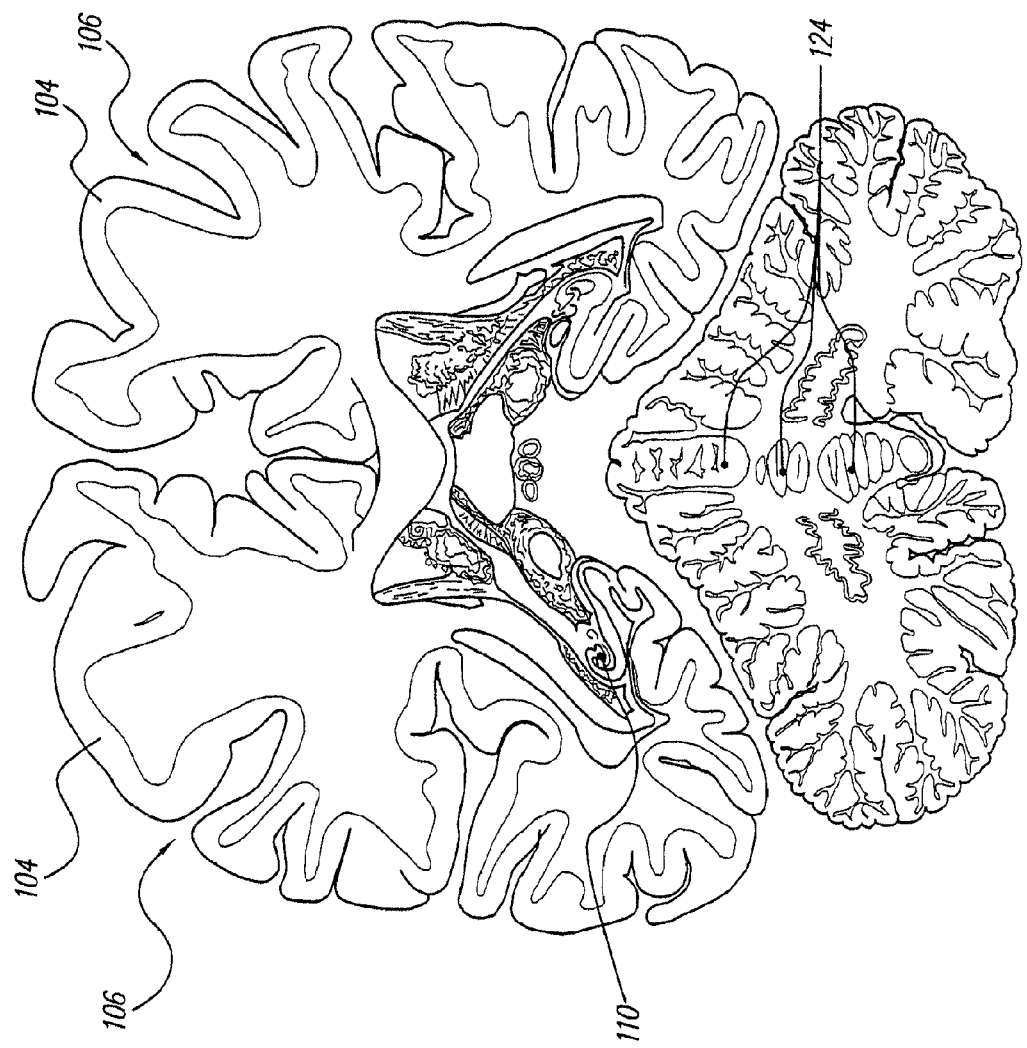

FIG. 1A depicts the lateral surface of the brain. FIG. 1B depicts, in a cross-sectional view, the medial surface of the head. FIGS. 1C-1F are coronal section views of the brain taken in cross-section along the lines indicated in FIG. 1B. FIG. 1A shows the motor cortex (104). As can be seen in FIG. 1A, the motor cortex (104) lies on the outermost region of the brain, along the top and sides of the skull, and is the most posterior portion of the frontal lobe, lying just anterior to the central sulcus (106) (also known as the central fissure). The motor cortex (104) is also shown in FIG. 1C, as is the hippocampus (110). FIG. 1D shows the anterior nucleus (114) and the ventral lateral nucleus (116). The centromedian nucleus (118) and locus coeruleus (120) are shown in FIG. 1E. FIG. 1F shows the cerebellum (124) and again shows the motor cortex (104), central sulcus (106), and hippocampus (110).

In some embodiments, at least one stimulus is applied with a system control unit (SCU) to the motor cortex (104) within the brain of a patient to treat and/or prevent one or more of the medical conditions described herein or a similar condition. As will be described in more detail below, because of the relative proximity of the motor cortex (104) to the skull, the SCU may be implanted adjacent to or within the motor cortex (104) with a minimal surgical procedure (e.g., through a small burr hole in the skull).

The stimulus applied to the motor cortex (104) may include electrical stimulation, also known as neuromodulation. Electrical stimulation will be described in more detail below. The stimulus may additionally or alternatively include drug stimulation. As will be described in more detail below, therapeutic dosages of one or more drugs may be infused into the motor cortex (104) or into a site near the motor cortex (104) to treat any of the medical conditions mentioned herein and similar medical conditions.

Figure 2:
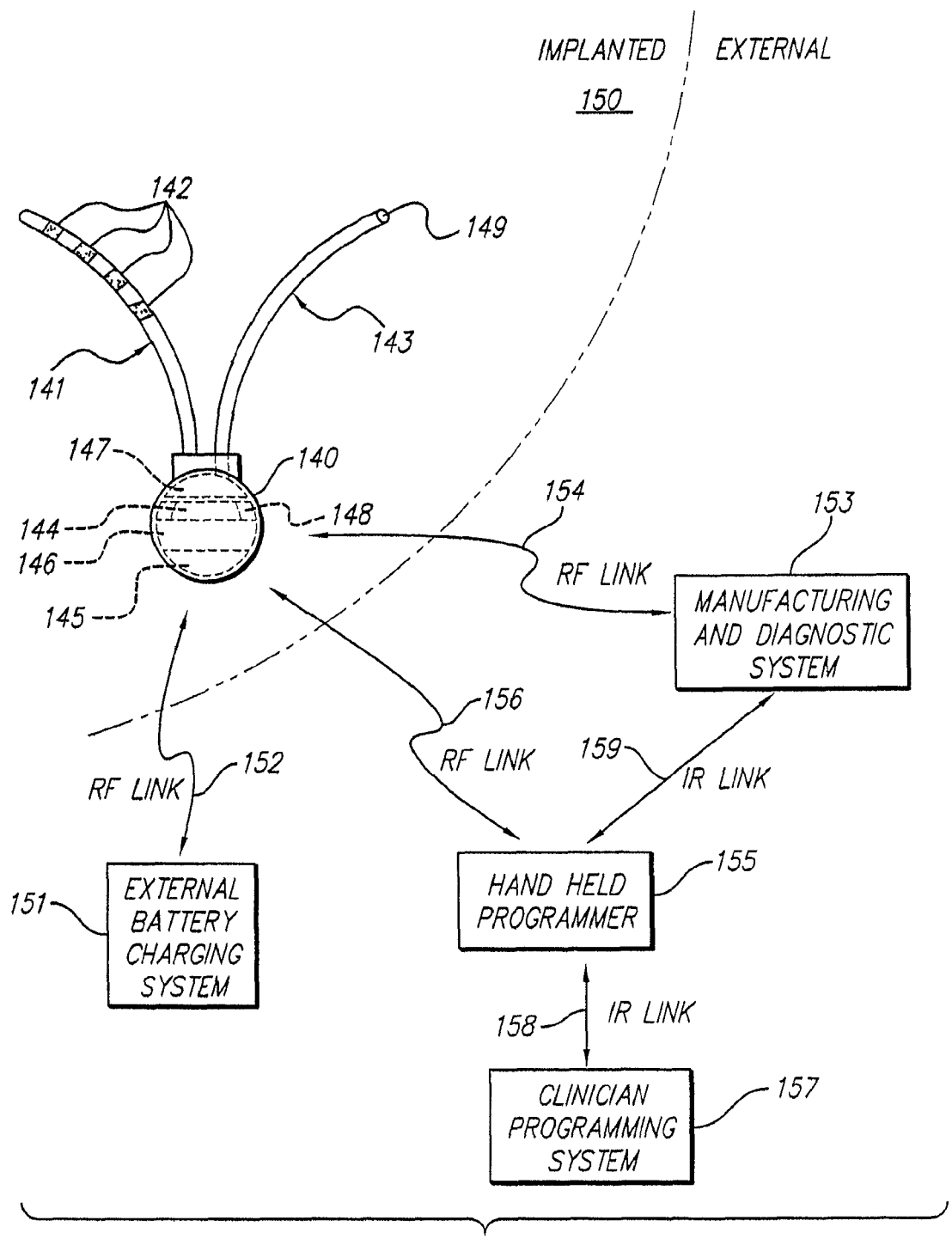
FIG. 2 illustrates an exemplary system control unit (SCU) that may be implanted within a patient and used to apply a stimulus to a target nerve to treat a particular medical condition according to principles described herein.

In some embodiments, the electrical stimulation and/or the drug stimulation may be performed by one or more implantable system control units (SCUs). FIG. 2 illustrates an exemplary SCU (140) that may be implanted within a patient (150) and used to apply a stimulus to the motor cortex (104; FIG. 1A) to treat a particular medical condition. As indicated above, the stimulus may be, for example, an electrical stimulation to the motor cortex (104; FIG. 1A), an infusion of one or more drugs into the motor cortex (104; FIG. 1A), or both. In general, the SCU (140) may be any relatively small implantable device configured to apply electrical and/or drug stimulation to the motor cortex (104; FIG. 1A). However, it will be recognized that the SCU (140) may be of any size as best serves a particular application.

FIG. 2 shows a lead (141) having a proximal end that may be coupled to the SCU (140) and that may include a number of electrodes (142) configured to apply a stimulation current to the motor cortex (104; FIG. 1A). In some embodiments, the lead (141) includes anywhere between two and sixteen electrodes (142). However, the lead (141) may include any number of electrodes (142) as best serves a particular application. The electrodes (142) may be arranged as an array, for example, having at least two or at least four collinear electrodes. In some embodiments, the electrodes are alternatively inductively coupled to the SCU (140). The lead (141) may be thin (e.g., less than 3 millimeters in diameter) such that the lead (141) may be positioned near the motor cortex (104; FIG. 1A), for example. The lead may additionally or alternatively be in the form of a substantially round electrode array with any number of electrode contacts to allow reprogramming of the current path and easy placement through a substantially round craniotomy hole. Alternatively, as will be described in more detail below, the SCU (140) may be leadless.

As illustrated in FIG. 2, the SCU (140) may include a number of components. A power source (145) is configured to output voltage used to supply the various components within the SCU (140) with power. The power source (145) may be a primary battery, a rechargeable battery, a capacitor, or any other suitable power source. A coil (148) is configured to receive and/or emit a magnetic field (also referred to as a radio frequency (RF) field) that is used to communicate with or receive power from one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the SCU (140) via one or more RF links (154, 156). One or more of these external devices (153, 155, 157) may also be used to control the infusion of one or more drugs into the motor cortex (104; FIG. 1A) to treat a particular medical condition.

Additionally, if multiple external devices are used in the treatment of a patient, there may be some communication among those external devices, as well as with the implanted SCU (140). For example, the CPS (157) may communicate with the HHP (155) via an infrared (IR) link (158) or via any other suitable communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the SCU (140). Furthermore, it will be recognized that the functions performed by the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like.

The SCU (140) may also include electrical circuitry (144) configured to produce electrical stimulation pulses that are delivered to the motor cortex (104; FIG. 1A) via the electrodes (142). In some embodiments, the SCU (140) may be configured to produce monopolar stimulation. The SCU (140) may alternatively or additionally be configured to produce bipolar stimulation. Monopolar electrical stimulation is achieved, for example, using the stimulator case as an indifferent electrode. Bipolar electrical stimulation is achieved, for example, using one of the electrodes of the electrode array as an indifferent electrode. The electrical circuitry (144) may include one or more processors configured to decode stimulation parameters and generate the stimulation pulses. In some embodiments, the SCU (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The SCU (140) may also include a programmable memory unit (146) for storing one or more sets of data and/or stimulation parameters. The stimulation parameters may include, but are not limited to, electrical stimulation parameters and drug stimulation parameters. The programmable memory (146) allows a patient, clinician, or other user of the SCU (140) to adjust the stimulation parameters such that the electrical stimulation and/or drug stimulation are at levels that are safe and efficacious for a particular medical condition and/or for a particular patient. Electrical stimulation and drug stimulation parameters may be controlled independently. However, in some instances, the electrical stimulation and drug stimulation parameters are coupled, e.g., electrical stimulation may be programmed to occur only during drug stimulation. The programmable memory (146) may be any type of memory unit such as, but not limited to, random access memory (RAM), static RAM (SRAM), a hard drive, or the like.

The electrical stimulation parameters may control various parameters of the stimulation current applied to the motor cortex (104; FIG. 1A) including, but not limited to, the frequency, pulse width, amplitude, burst pattern (e.g., burst on time and burst off time), duty cycle or burst repeat interval, ramp on time and ramp off time of the stimulation current that is applied to the motor cortex (104; FIG. 1A). The drug stimulation parameters may control various parameters including, but not limited to, the amount of drugs infused into the motor cortex (104; FIG. 1A), the rate of drug infusion, and the frequency of drug infusion.

Specific electrical stimulation and drug stimulation parameters may have different effects on different types of medical conditions and/or neural tissue. Thus, in some embodiments, the electrical stimulation and/or drug stimulation parameters may be adjusted by the patient, a clinician, or other user of the SCU (140) as best serves a particular medical condition. Furthermore, the electrical stimulation and/or drug stimulation parameters may be adjusted to target specific neural populations and to exclude others. The electrical stimulation and/or drug stimulation parameters may also be automatically adjusted by the SCU (140), as will be described below. For example, the SCU (140) may increase excitement of neural tissue within the motor cortex (104; FIG. 1A) by applying a stimulation current having a relatively low frequency to the motor cortex (104; FIG. 1A) (e.g., less than 100 Hz). The SCU (140) may also decrease excitement of neural tissue within the motor cortex (104; FIG. 1A) by applying a relatively high frequency to the motor cortex (104; FIG. 1A) (e.g., greater than 100 Hz). The SCU (140) may also be programmed to apply the stimulation current to the motor cortex (104; FIG. 1A) intermittently or continuously.

As shown in FIG. 2, a pump (147) may also be included within the SCU (140). The pump (147) is configured to store and dispense one or more drugs, for example, through a catheter (143). The catheter (143) is coupled at a proximal end to the SCU (140) and may have an infusion outlet (149) for infusing dosages of the one or more drugs into a predetermined site within the motor cortex (104; FIG. 1A). In some embodiments, the SCU (140) may include multiple catheters (143) and/or pumps (147) for storing and infusing dosages of the one or more drugs into predetermined sites within the motor cortex (104; FIG. 1A).

The SCU (140) of FIG. 2 is illustrative of many types of SCUs that may be used to apply electrical stimulation to the motor cortex (104; FIG. 1A) and/or infuse one or more drugs into the motor cortex (104; FIG. 1A) to treat a particular medical condition. For example, the SCU (140) may include an implantable pulse generator (LPG) coupled to one or more leads (141) having a number of electrodes (142). In the case of drug stimulation only, the SCU (140) comprises a pump. Alternatively, the SCU (140) may be an implantable microstimulator, such as a BION® microstimulator (Advanced Bionics® Corporation, Valencia, Calif.). The following listed patents describe various details associated with the manufacture, operation, and use of BION implantable micro stimulators, and are all incorporated herein by reference in their respective entireties:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 6,185,452 | Issued Feb. 6, 2001 | Battery-Powered Patient Implantable Device |
| U.S. Pat. No. 6,164,284 | Issued Dec. 26, 2000 | System of Implantable Devices For Monitoring and/or Affecting Body Parameters |
| U.S. Pat. No. 6,208,894 | Issued Mar. 27, 2001 | System of Implantable Devices For Monitoring and/or Affecting Body Parameters |
| U.S. Pat. No. 6,051,017 | Issued Apr. 18, 2000 | Implantable Microstimulator and Systems Employing Same |

Figure 3:
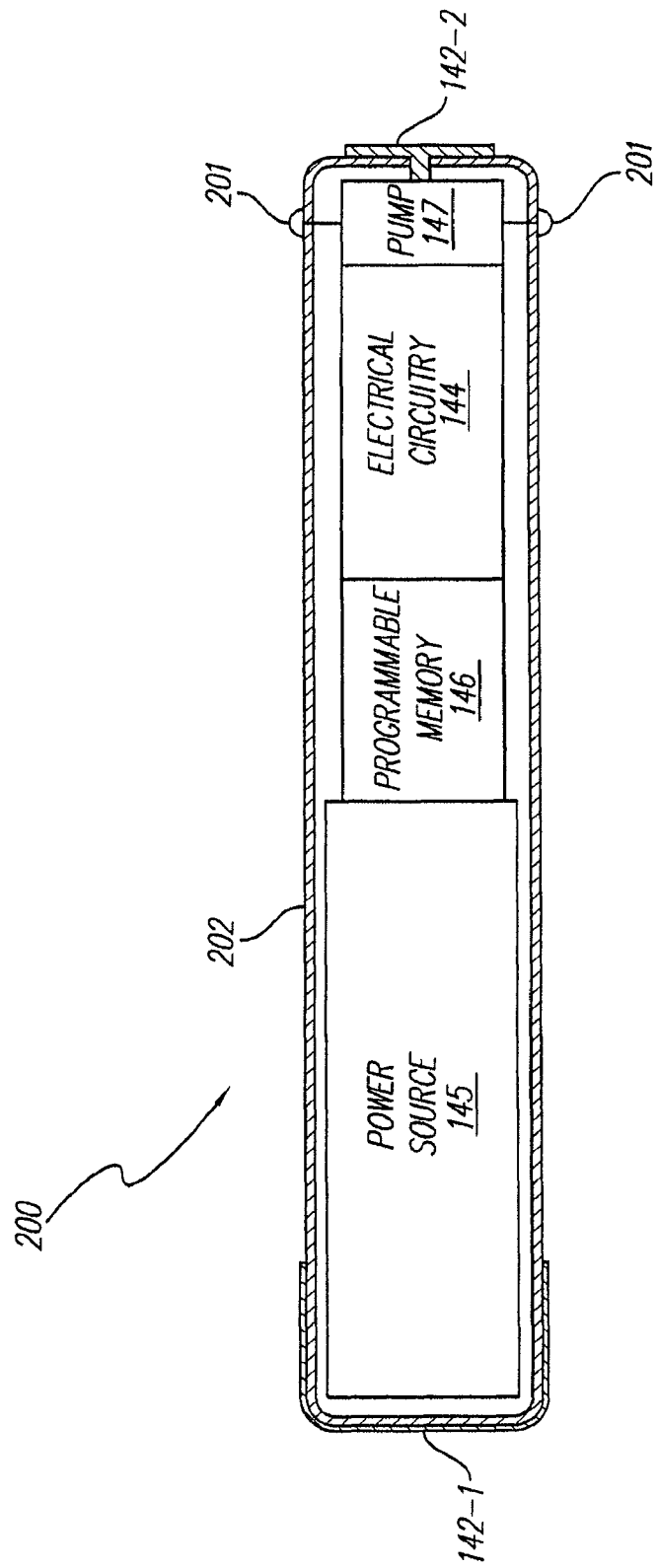
FIG. 3 illustrates an exemplary BION microstimulator that may be used as the SCU according to principles described herein.

FIG. 3 illustrates an exemplary BION microstimulator (200) that may be used as the SCU (140; FIG. 2) described herein. Other configurations of the microstimulator (200) are possible, as shown in the above-referenced patents and as described further below.

As shown in FIG. 3, the microstimulator (200) may include the power source (145), the programmable memory (146), the electrical circuitry (144), and the pump (147) described in connection with FIG. 2. These components are housed within a capsule (202). The capsule (202) may be a thin, elongated cylinder or any other shape as best serves a particular application. The shape of the capsule (202) may be determined by the structure of the desired target nerve, the surrounding area, and the method of implementation.

In some embodiments, the microstimulator (200) may include two or more leadless electrodes (142). Either or both of the electrodes (142) may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the microstimulator (200), while allowing most elements of the microstimulator (200) to be located in a more surgically convenient site. This minimizes the distance traversed and the surgical planes crossed by the microstimulator (200) and any lead(s).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

As shown in FIG. 3, the microstimulator (200) may include one or more infusion outlets (201). The infusion outlets (201) facilitate the infusion of one or more drugs into a treatment site to treat a particular medical condition. The infusion outlets (201) may dispense one or drugs directly to the treatment site. Alternatively, as will be described in more detail below, catheters may be coupled to the infusion outlets (201) to deliver the drug therapy to a treatment site some distance from the body of the microstimulator (200). The stimulator (200) of FIG. 3 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

Figure 4:
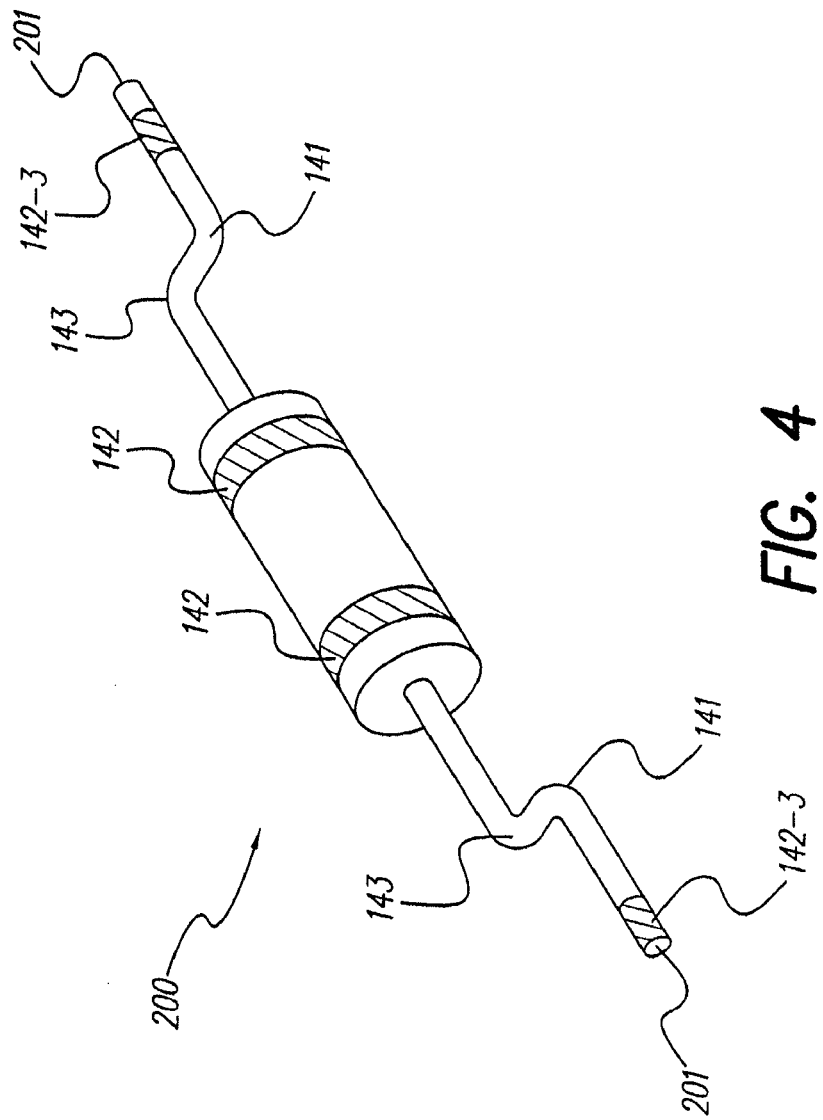
FIG. 4 shows that one or more catheters may be coupled to the microstimulator according to principles described herein.

FIG. 4 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the end of each catheter (143). Thus, in the example of FIG. 4, a drug therapy is expelled by the pump (147, FIG. 4) from an infusion outlet (201, FIG. 4) in the casing (202, FIG. 4) of the microstimulator (200), through the catheter (143), out an infusion outlet (201) at the end of the catheter (143) to the target site within the patient. As shown in FIG. 4, the catheters (143) may also serve as leads (141) having one or more electrodes (142-3) disposed thereon. Thus, the catheters (143) and leads (141) of FIG. 4 permit infused drugs and/or electrical stimulation to be directed to a treatment site while allowing most elements of the microstimulator (200) to be located in a more surgically convenient site. The example of FIG. 4 may also include leadless electrodes (142) disposed on the housing of the microstimulator (200), in the same manner described above.

Returning to FIG. 2, the SCU (140) may be configured to operate independently. Alternatively, the SCU (140) may be configured to operate in a coordinated manner with one or more additional SCUs (140), other implanted devices, or other devices external to the patient's body. For instance, a first SCU (140) may control or operate under the control of a second SCU (140), other implanted device, or other device external to the patient's body. The SCU (140) may be configured to communicate with other implanted SCUs (140), other implanted devices, or other devices external to the patient's body via an RF link, an untrasonic link, an optical link, or any other type of communication link. For example, the SCU (140) may be configured to communicate with an external remote control that is capable of sending commands and/or data to the SCU (140) and that is configured to receive commands and/or data from the SCU (140).

In order to determine the amount and/or type(s) of stimulating drug(s) and/or the strength and/or duration of electrical stimulation required to most effectively treat a particular medical condition, various indicators of the medical condition and/or a patient's response to treatment may be sensed or measured. These indicators may include, but are not limited to, symptoms related to movement disorders, muscle or limb activity (e.g., electromyography (EMG)), electrical activity of the brain (e.g., EEG), neurotransmitter levels, hormone levels, and/or medication levels. In some embodiments, the SCU (140) may be configured to change the stimulation parameters in a closed loop manner in response to these measurements. The SCU (140) may be configured to perform the measurements. Alternatively, other sensing devices may be configured to perform the measurements and transmit the measured values to the SCU (140).

Thus, it is seen that one or more external appliances may be provided to interact with the SCU (140), and may be used to accomplish at least one or more of the following functions:

Function 1: If necessary, transmit electrical power to the SCU (140) in order to power the SCU (140) and/or recharge the power source (145).

Function 2: Transmit data to the SCU (140) in order to change the stimulation parameters used by the SCU (140).

Function 3: Receive data indicating the state of the SCU (140) (e.g., battery level, drug level, stimulation parameters, etc.).

Additional functions may include adjusting the stimulation parameters based on information sensed by the SCU (140) or by other sensing devices.

By way of example, an exemplary method of treating a particular medical condition within a patient may be carried out according to the following sequence of procedures. The steps listed below may be modified, reordered, and/or added to as best serves a particular application.

1. An SCU (140) is implanted so that its electrodes (142) and/or infusion outlet (149) are coupled to or located near the motor cortex (104; FIG. 1A). If the SCU (140) is a microstimulator, such as the BION microstimulator (200; FIG. 3), the microstimulator itself may be coupled to the motor cortex (104; FIG. 1A).

2. The SCU (140) is programmed to apply at least one stimulus to the motor cortex (104; FIG. 1A). The stimulus may include electrical stimulation and/or drug stimulation.

3. When the patient desires to invoke electrical and/or drug stimulation, the patient sends a command to the SCU (140) (e.g., via a remote control) such that the SCU (140) delivers the prescribed electrical and/or drug stimulation. The SCU (140) may be alternatively or additionally configured to automatically apply the electrical and/or drug stimulation in response to sensed indicators of the particular medical condition.

4. To cease electrical and/or drug stimulation, the patient may turn off the SCU (140) (e.g., via a remote control).

5. Periodically, the power source (145) of the SCU (140) is recharged, if necessary, in accordance with Function 1 described above.

For the treatment of any of the various types of medical conditions, it may be desirable to modify or adjust the algorithmic functions performed by the implanted and/or external components, as well as the surgical approaches. For example, in some situations, it may be desirable to employ more than one SCU (140), each of which could be separately controlled by means of a digital address. Multiple channels and/or multiple patterns of electrical and/or drug stimulation may thereby be used to deal with multiple medical conditions.

Figure 5:
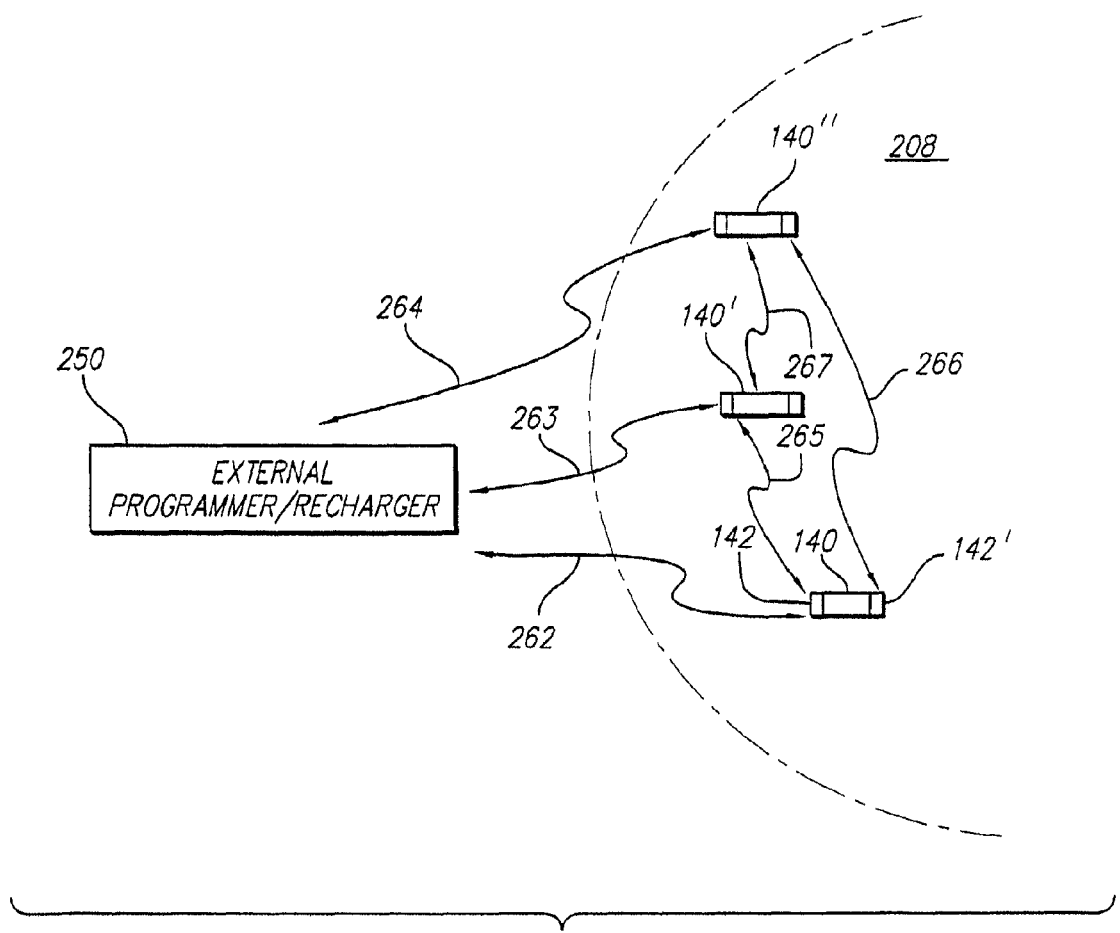
FIG. 5 depicts a number of SCUs configured to communicate with each other and/or with one or more external devices according to principles described herein.

For instance, as shown in the example of FIG. 5, a first SCU (140) implanted beneath the skin of the patient (208) provides a stimulus to a first location; a second SCU (140') provides a stimulus to a second location; and a third SCU (140") provides a stimulus to a third location. The first, second, and third locations may be various locations adjacent to the motor cortex (104; FIG. 1A) or throughout the body of the patient (208). As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. SCU (140), may control or operate under the control of another implanted device(s), e.g. SCU (140') and/or SCU (140"). Control lines (262-267) have been drawn in FIG. 5 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple SCUs (140) operating in a coordinated manner, the first and second SCUs (140, 140') of FIG. 5 may be located at various locations throughout the body (208) and configured to sense various indicators of a particular medical condition and transmit the measured information to the third SCU (140"). The third SCU (140") may then use the measured information to adjust its stimulation parameters and apply electrical and/or drug stimulation to the motor cortex (104; FIG. 1A) accordingly.

Alternatively, the external device (250) or other external devices communicating with the external device may be configured to sense various indicators of a patient's condition. The sensed indicators can then be transmitted to the external device (250) or to one or more of the implanted SCUs which may adjust stimulation parameters accordingly. In other examples, the external controller (250) may determine whether any change to stimulation parameters is needed based on the sensed indicators. The external device (250) may then signal a command to one or more of the SCUs to adjust stimulation parameters accordingly.

As mentioned, the SCU (140) of FIG. 2 may be implanted within the patient using any suitable surgical procedure such as, but not limited to, injection via a small hole (e.g., burr hole) through the skull, small incision, open placement, laparoscopy, or endoscopy. One or more surgical tools may be used to implant the SCU (140) such as, but not limited to, a hypodermic needle, bore needle, or any other tool specially designed for the purpose. In some instances, the SCU (140) may be implanted at a site that is relatively close or adjacent to the motor cortex (104; FIG. 1A) with the lead (141) and/or the catheter (143) being routed to the motor cortex (104; FIG. 1A).

Figure 6:
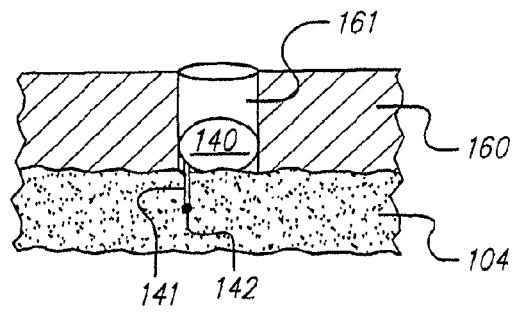
FIG. 6 shows an SCU implanted in the skull adjacent to the motor cortex according to principles described herein.

For example, FIG. 6 shows an SCU (140) implanted in the skull (160) adjacent to the motor cortex (104). As shown in FIG. 6, the SCU (140) may be implanted via a hole (161) that is created in the skull (160). The hole (161) may be a burr hole or any other suitable hole and may be created by drilling or by another suitable method. The hole (161) may be of a suitable diameter or size and extend all the way through the skull (160) such that the motor cortex (104) is easily accessed. The SCU (140) may be placed within the hole (161) and coupled to the walls of the hole (161) and/or the top surface of the motor cortex (104) using a suitable adhesive. Once the SCU (140) has been implanted, the hole (161) may be covered by an appropriately sized cap (not shown).

As shown in FIG. 6, a lead (141) may be coupled to the SCU (140) with the distal end of the lead (141) being routed to a particular location within the motor cortex (104). The distal end of the lead (141) may include one or more electrodes (142) for delivering electrical stimulation to the motor cortex (104). As described and illustrated above, a catheter (143) may also or alternatively be coupled to the SCU (140) and routed to the motor cortex (104) for delivering drug stimulation to the motor cortex (104). In some alternative embodiments, the hole (161) only extends partially into the skull (160). In these embodiments, a much smaller hole then extends from the main hole (151) to the interior of the skull (160). The lead (141) and/or a catheter is then routed through this smaller hole in the skull (160) to the motor cortex (104).

Figure 7A:
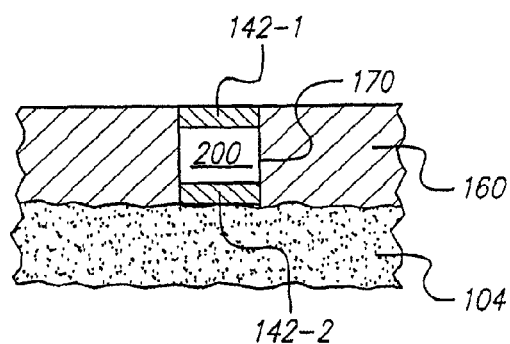
FIGS. 7A-7C shows multiple configurations of a microstimulator SCU that has been inserted into a hole of the skull having substantially the same size as the microstimulator according to principles described herein.
Figure 7B:
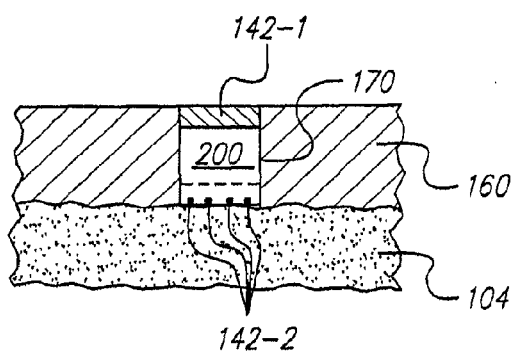
Figure 7C:
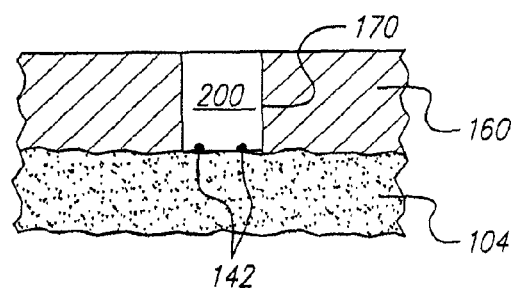

In some embodiments, a hole substantially equal to the exact size of the SCU (140) may be created in the skull (160) and the SCU (140) may be used to fill this hole while still being in a position to provide extradural stimulation of the motor cortex (104). For example, FIGS. 7A-7C show exemplary microstimulator SCUs (200) that have been inserted into a hole (170) of the skull (160) having substantially the same size as the microstimulator (200). As shown in FIG. 7A-7C, the microstimulator (200) fills the hole (170) created in the skull (160) and may be affixed to the walls of the hole (170) using a suitable adhesive.

FIG. 7A shows that a distal end of the microstimulator (200) having a stimulating electrode (142-2) may be coupled to the outer surface of the motor cortex (104) to provide electrical stimulation to the motor cortex (104). A proximal end of the microstimulator (200) having an indifferent or grounding electrode (142-1) is located near the outer surface of the skull (160).

FIG. 7B shows an alternative embodiment wherein the distal end of the microstimulator (200) has multiple stimulating electrodes (142-2) for providing electrical stimulation to the motor cortex (104). The multiple stimulating electrodes (142-2) are coupled to the outer surface of the motor cortex (104). The proximal end of the microstimulator (200) having an indifferent or grounding electrode (142-1) is located near the outer surface of the skull (160).

FIG. 7C shows yet another alternative embodiment wherein all of the electrodes (142) of the microstimulator (200) are coupled to the outer surface of the motor cortex (104) to provide electrical stimulation to the motor cortex (104). One or more of the multiple electrodes (142) may be stimulating electrodes and one or more of the multiple electrodes (142) may be indifferent electrodes.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with a medical condition, comprising
    implanting a microstimulator within an opening extending completely through a skull of said patient, wherein the microstimulator resides within the opening, wherein said microstimulator comprises a capsule, and one or both of electrical circuitry and a drug pump contained within said capsule;
    generating a stimulus in accordance with one or more stimulation parameters using said microstimulator; and
    applying said stimulus to a portion of a motor cortex of said patient adjacent said opening, thereby treating said medical condition, wherein sad microstimulator comprises the electrical circuitry contained within said capsule, and a stimulation electrode disposed on an external surface of said capsule, wherein said stimulus is extradurally applied to said motor cortex
    and wherein said microstimulator comprises an indifferent electrode disposed on said external surface of said capsule, and said microstimulator is implanted within said opening, such that said stimulation electrode is adjacent said motor cortex and said indifferent electrode is adjacent an outer surface of said skull.

* * * * *